US00PP30872P2

(12) United States Plant Patent
Van Swieten

(10) Patent No.: US PP30,872 P2
(45) Date of Patent: Sep. 3, 2019

(54) ***PHALAENOPSIS* ORCHID PLANT NAMED 'PHALGAQXYK'**

(50) Latin Name: ***Phalaenopsis* hybrid**
Varietal Denomination: PHALGAQXYK

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/350,369

(22) Filed: Nov. 9, 2018

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ..... A01H 5/02; A01H 6/62
See application file for complete search history.

*Primary Examiner* — Annette H Para
(74) *Attorney, Agent, or Firm* — Jondle & Associates, P.C.

(57) ABSTRACT

A new and distinct variety of *Phalaenopsis* plant named 'PHALGAQXYK', particularly characterized by having light purple flowers with reddish-purple shade and light purple lips, 1 to 3 peduncles that are long and sturdy, leaves that are narrow oblong, and is propagated by meristem tissue culture, is disclosed.

3 Drawing Sheets

Genus and species: *Phalaenopsis* hybrid.
Variety denomination: 'PHALGAQXYK'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGAQXYK'.

The new *Phalaenopsis* plant is a product of a planned breeding program conducted by the inventor in Bleiswijk, The Netherlands. The objective of this breeding program was to create a new *Phalaenopsis* plant with numerous attractive light purple flowers with reddish-purple shade and light purple lips, suitable for potted plant production.

The new *Phalaenopsis* plant 'PHALGAQXYK' is a result of cross-pollination made by the inventor in June 2009 in Bleiswijk, The Netherlands, of the proprietary female, or seed parent, *Phalaenopsis* hybrid '23426-01' (unpatented) with the proprietary male, or pollen parent, *Phalaenopsis* hybrid '4347-01' (unpatented).

The new *Phalaenopsis* was selected by the inventor as a single plant within the progeny of the stated cross-pollination in a controlled greenhouse in Bleiswijk, The Netherlands, in June 2012. Asexual reproduction of the new *Phalaenopsis* plant by meristem tissue culture since 2015 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 24, 2017. 'PHALGAQXYK' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands, and can be used to distinguish 'PHALGAQXYK' as a new and distinct variety of *Phalaenopsis* plant.

1) Light purple flowers with reddish-purple shade and light purple lips;
2) 1 to 3 peduncles;
3) Peduncle is long and sturdy; and
4) Shape of the leaf is narrow oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week old plants in August 2018. Colors in the photographs may differ from the color values cited in the detailed botanical description, which accurately describe the actual colors of the new variety.

DESCRIPTION OF THE NEW VARIETY

Figure 1:
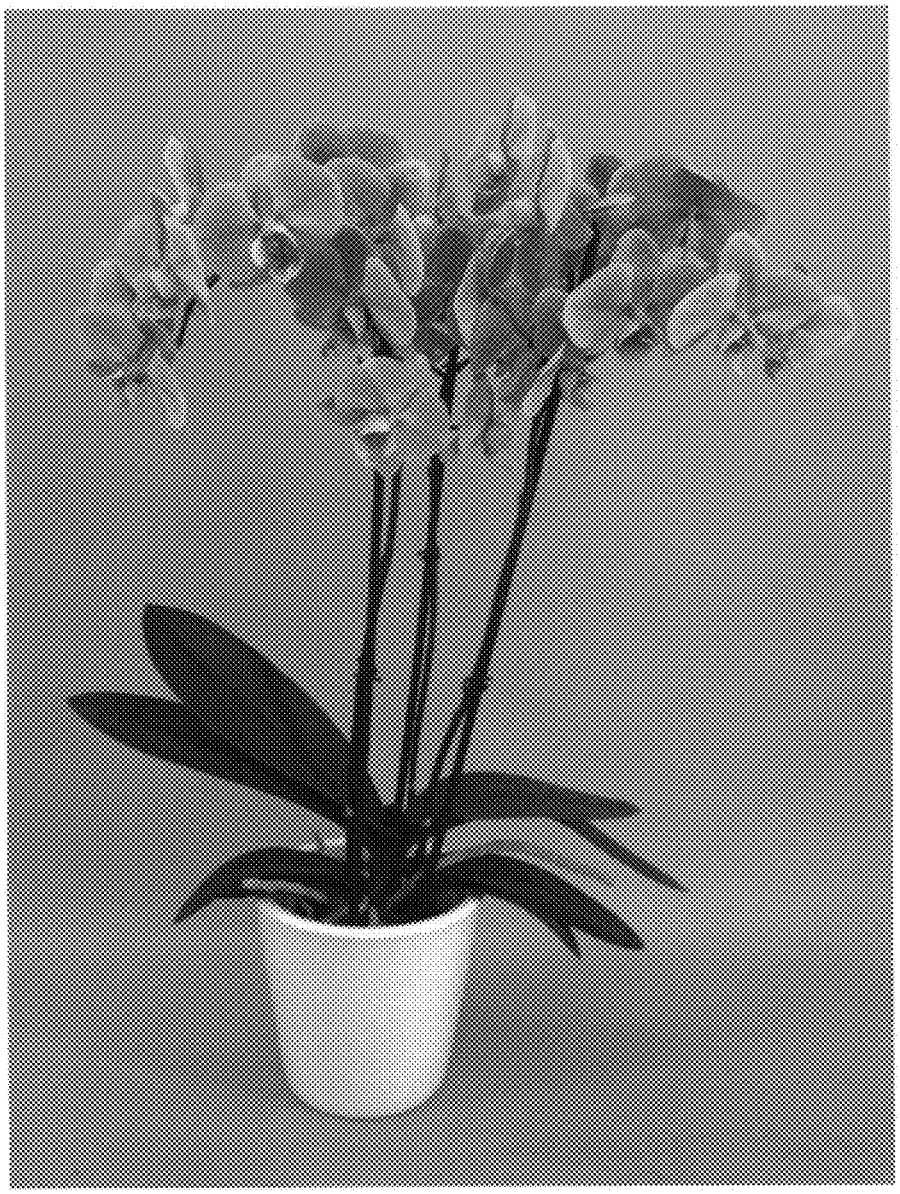
FIG. 1 shows the overall plant habit, including blooms and foliage of 'PHALGAQXYK'.
Figure 2:
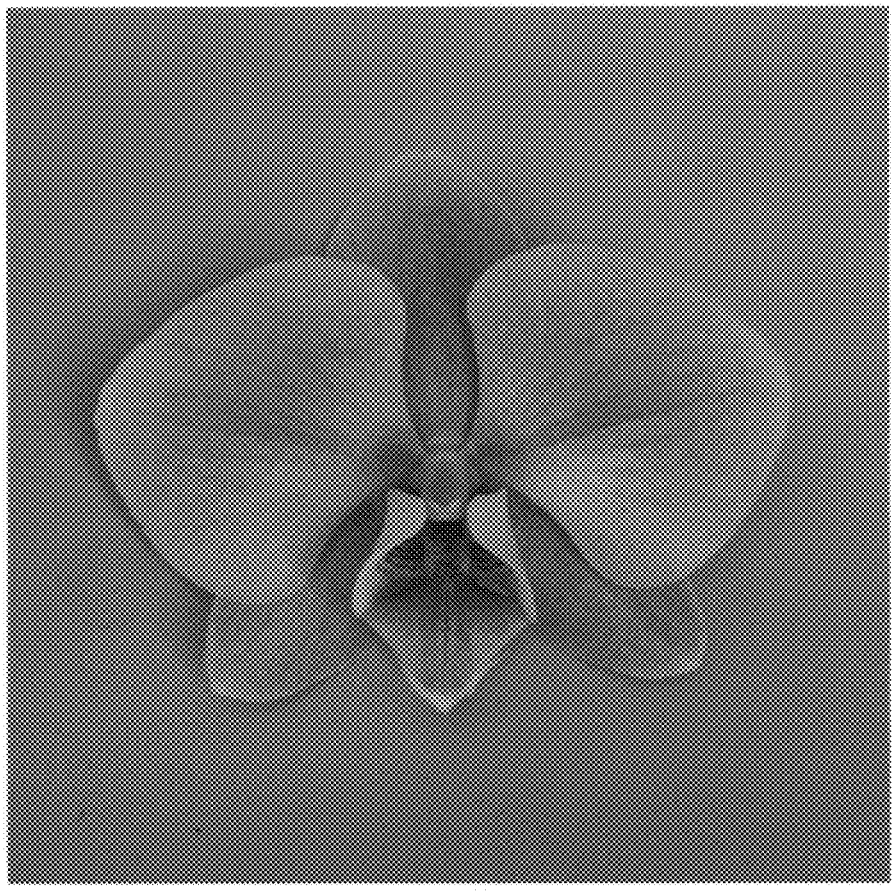
FIG. 2 shows a close-up of a flower of 'PHALGAQXYK'.
Figure 3:
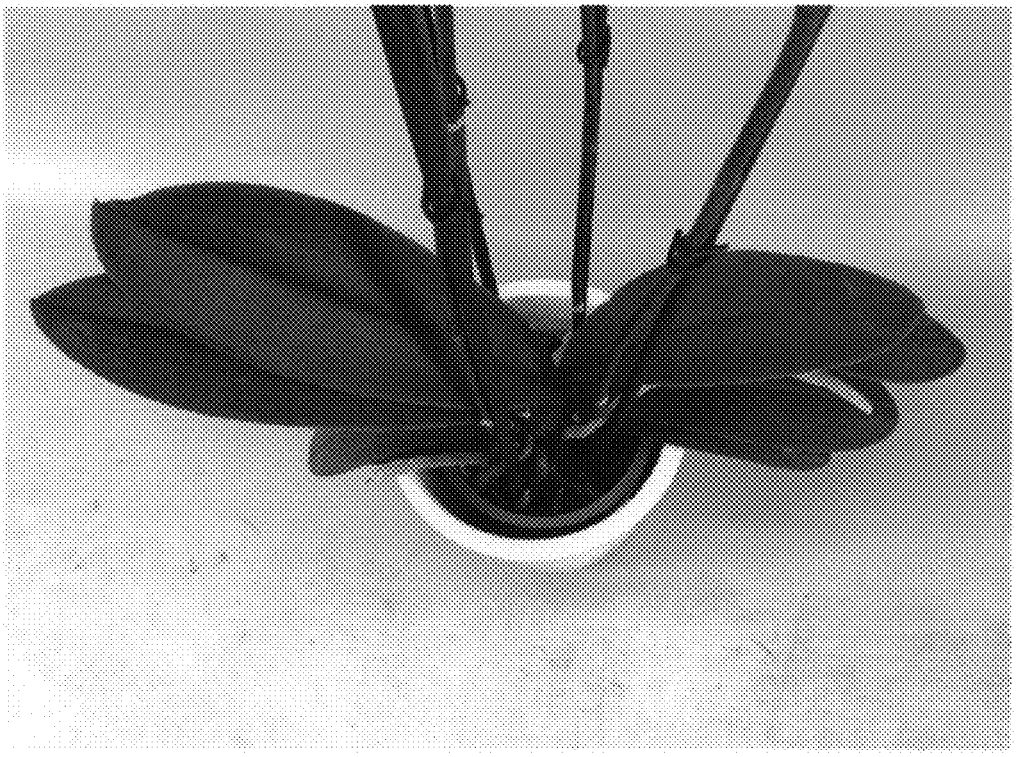
FIG. 3 shows an overhead view of the leaves of 'PHALGAQXYK'.

The following detailed description sets forth the distinctive characteristics of 'PHALGAQXYK'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in August 2018 on flowering plants which were planted in 12 centimeter (diameter) pots. After in-vitro propagation, the plants were grown in nursery trays for 20-24 weeks, followed by transplantation to 12 centimeter (diameter) pots and grown in a greenhouse between 27° C. to 29° C. for 30 weeks, continued by a cooling period of 8 weeks between 18° C. to 20° C. and 12 weeks in a greenhouse of 21° C. Flowering occurs after 50-weeks in 12 centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGAQXYK'.

Parentage:

*Female parent*.—*Phalaenopsis* cultivar '23426-01' (unpatented).

*Male parent*.—*Phalaenopsis* cultivar '4347-01' (unpatented).

Propagation:

*Type*.—Meristem tissue culture.

Roots:

*Root description*.—Greyed-green colored roots (RHS 190B to 190C) with branching lateral roots having dark purplish-red (RHS N79B) colored root tips on one side and green (RHS 144B) colored root tips on the other side.

Plant:

*Commercial crop time to flowering*.—Following asexual propagation (in-vitro), the rooted cuttings grow for 20-24 weeks. After transplantation into 12 cm pots, the plants are finished after 48 to 50 weeks.

*Growth habit of peduncle*.—Upright to slightly pendant with panicle inflorescence.

*Height (from soil level to top of inflorescence)*.—Approximately 50.0 cm to 55.0 cm.

*Width (measured from leaf tips)*.—About 41.0 cm to 43.0 cm.

*Vigor*.—Moderate.

Leaves:

*Mature leaves*.—Quantity per plant: 8 to 9 leaves are produced before flowering. Length (fully expanded): 20.0 cm to 22.0 cm. Width: 6.0 cm to 7.0 cm. Shape: Narrow oblong. Base shape: Moderately elongated. Apex: Obtuse unequal. Leaf blade angle with the petiole (measured from the horizontal position): Between 25 degrees and 40 degrees. Leaf margin: Entire. Color: Upper surface: RHS 147A and slightly mottled toward the tip. Lower surface: RHS 147B; dark red (RHS 187A) toward the tip and margin. Texture (upper surface): Rough. Thickness: 1.9 mm to 2.2 mm. Venation: Pattern: Parallel. Color of the midvein: Upper surface: RHS 147A. Lower surface: RHS 147B.

Peduncle:

*Quantity per plant*.—1 to 3.

*Number of flowers per peduncle*.—10 to 16.

*Length*.—50.0 cm to 55.0 cm.

*Diameter*.—4.9 mm to 5.3 mm.

*Strength*.—Strong.

*Aspect*.—Upright to slightly pendant.

*Texture*.—Smooth.

*Color*.—Mix of brown (RHS 200B) and green (RHS 146C).

*Internode length*.—5.0 cm to 6.0 cm.

*Callosities*.—None.

Inflorescence description:

*Appearance*.—Upright to slightly pendant, panicle inflorescence with bilaterally symmetrical flowers that open in succession beginning with the lowermost flower.

*Inflorescence size*.—Height (from base to tip): 180.0 mm to 230.0 mm.

*Flowering time*.—First flowers can be expected 10 to 11 months after planting in a 12 cm (diameter) pot.

*Flower*.—Height: 63.0 mm to 68.0 mm. Diameter: 83.0 mm to 88.0 mm. Depth of lip: 21.0 mm to 23.0 mm.

*Flower longevity*.—On the plant: 13 to 19 weeks.

*Fragrance*.—Absent.

*Flower bud*.—Average size: Large. Length: 24.0 mm to 26.0 mm. Width: 19.0 mm to 21.0 mm. Shape: Egg shaped. Color: Red-purple (mix of RHS N77B and N79C).

*Petals*.—Arrangement: Open/free. Shape: Semi-circular. Apex: Rounded asymmetric. Margin: Slightly undulated. Length (from base to tip): 39.0 mm to 41.0 mm. Width: 43.0 mm to 45.0 mm. Color (when fully opened): Upper surface: Basic color: Very light purple (RHS 76B to 76C). Over color: Reddish-purple shade (RHS N78D) and center (RHS N78B). Lower surface: Basic color: Very light purple (RHS N78C). Over color: Reddish-purple shade (RHS N78D) and center (RHS N78B).

*Dorsal sepal*.—Shape: Elliptic. Apex: Rounded emarginated. Margin: Entire. Length (from base to tip): 39.0 mm to 41.0 mm. Width: 27.0 mm to 29.0 mm. Color (when fully opened): Upper surface: Basic color: Purplish-pink (RHS N78C). Over color: Light purple edge (RHS 76A). Lower surface: Basic color: Reddish-purple (RHS N78B). Over color: Reddish-purple (RHS N78D).

*Lateral sepals*.—Shape: Ovate. Apex: Obtuse asymmetric. Margin: Entire. Length (from base to tip): 40.0 mm to 42.0 mm. Width: 22.0 mm to 24.0 mm. Color (when fully opened): Upper surface: Basic color: Reddish-purple (RHS N78D). Over color: Slightly light yellow-green (RHS 145D) with purplish-red dots at the base (RHS 71A). Lower surface: Basic color: Reddish-purple (RHS N78D). Over color: Slightly very light purple (RHS 76B) at the base; reddish-purple middle vein (RHS N78B).

*Labellum (lip)*.—Whiskers: Present. Length of whiskers: 12.0 mm to 14.0 mm. Color of whiskers: Very light purple (RHS 76B) at the base and white (RHS NN155C) toward the tip. Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Undulated. Length: 19.0 mm to 21.0 mm. Width: 13.0 mm to 15.0 mm. Color: Yellow (RHS 15A) at the base with dark red stripes (RHS 187B); one side yellow-orange (RHS 163A and 163D); very light purple (RHS 76C) toward the edge with reddish-purple shade (RHS N78D).

*Apical lobe*.—Shape: Triangular. Margin: Entire. Length: 20.0 mm to 22.0 mm. Width: 21.0 mm to 23.0 mm. Color: Red (RHS 182B and 181A) at the base, dotted (RHS 183B); slightly light yellow wings (RHS 163D); very light purple (RHS 76B) toward whiskers.

*Callus*.—Average size: Medium. Height: 5.0 mm to 6.0 mm. Length: 5.0 mm to 6.0 mm. Width: 4.0 mm to 5.0 mm. Color: Yellow (RHS 14A), striped and dotted (RHS 183A).

Reproductive organs:

*Column*.—Length: 8.0 mm to 10.0 mm. Diameter: 5.8 mm to 6.0 mm. Color: Very light purple (RHS 76B) at the base with purplish-pink region (RHS N78C) toward the tip.

*Pollinia*.—Quantity: 2. Diameter: 1.1 mm to 1.3 mm. Color: Orange (RHS 26A).

*Ovary*.—Length: 10.0 mm to 12.0 mm. Diameter: 2.4 mm to 2.6 mm. Color: Very light purple (RHS 76B) toward the flower.

*Pedicel*.—Length: 37.0 mm to 39.0 mm. Diameter: 2.7 mm to 2.9 mm. Color: Dark red (RHS 187B) at the base; light green (RHS 195B) and very light purple (RHS 76B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGAQXYK' differs from female parent plant '23426-01' (unpatented) in that 'PHALGAQXYK' has whiskers that are very light purple at the base and white toward the tips, whereas '23426-01' has whiskers that are reddish-purple with yellow tips. Additionally, 'PHALGAQXYK' has shorter whiskers than '23426-01'.

'PHALGAQXYK' differs from male parent plant '4347-01' (unpatented) in that 'PHALGAQXYK' has a shaded flower pattern and whiskers that are very light purple at the base and white toward the tips, whereas '4347-01' has a striped flower pattern and whiskers that are deep red. Additionally, 'PHALGAQXYK' has longer whiskers than '4347-01'.

'PHALGAQXYK' is most similar to the commercial *Phalaenopsis* plants named 'PHALDESBIM' (U.S. Plant Pat. No. 27,671) and 'PHALCIMEI' (U.S. Plant Pat. No. 27,200). 'PHALGAQXYK' differs from the commercial variety 'PHALDESBIM' in that 'PHALGAQXYK' has narrow oblong shaped leaves, whereas 'PHALDESBIM' has obovate shaped leaves. Additionally, 'PHALGAQXYK' has longer leaves and shorter whiskers than 'PHALDESBIM'.

'PHALGAQXYK' differs from the commercial variety 'PHALCIMEI' in that 'PHALGAQXYK' has obtuse unequal leaf apexes, whereas 'PHALCIMEI' has unequal mucronate leaf apexes. Additionally, 'PHALGAQXYK' has shorter leaves and longer whiskers than 'PHALCIMEI'.

I claim:

1. A new and distinct variety of *Phalaenopsis* plant named 'PHALGAQXYK', substantially as described and illustrated herein.

* * * * *